United States Patent [19]

Schnegg et al.

[11] 4,276,431
[45] Jun. 30, 1981

[54] PROCESS FOR THE PREPARATION OF ALKALI METAL SALTS OF HYDROXYBENZOATES, WHICH ARE SUBSTANTIALLY ANHYDROUS AND FREE FROM HYDROXYBENZOIC ACID

[75] Inventors: Peter Schnegg, Odenthal; Walter Rapp, Leverkusen; Bernhard Vosteen, Cologne, all of Fed. Rep. of Germany

[73] Assignee: Bayer Aktiengesellschaft, Leverkusen, Fed. Rep. of Germany

[21] Appl. No.: 77,445

[22] Filed: Sep. 20, 1979

[30] Foreign Application Priority Data

Sep. 30, 1978 [DE] Fed. Rep. of Germany ....... 2842807
Apr. 27, 1979 [DE] Fed. Rep. of Germany ....... 2917273

[51] Int. Cl.³ ............................................ C07C 69/88
[52] U.S. Cl. ...................................... 560/67; 560/45; 560/46; 560/42; 560/56; 560/59
[58] Field of Search ...................... 560/67, 45, 46, 42, 560/56, 59

[56] References Cited

U.S. PATENT DOCUMENTS 2,312,001 2/1943 Sabalitschke ...................... 560/67 X
3,714,227 1/1973 Ueno et al. ........................ 560/67 X

FOREIGN PATENT DOCUMENTS 704464 2/1965 Canada ..................................... 560/67

*Primary Examiner*—Paul J. Killos
*Attorney, Agent, or Firm*—Sprung, Felfe, Horn, Lynch & Kramer

[57] ABSTRACT

Alkali metal salts of hydroxybenzoates are claimed which are substantially anhydrous and free from hydrobenzoic acid and have the formula

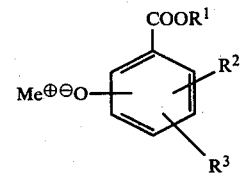

in which
$R^1$ denotes alkyl, alkenyl, cycloalkyl or aralkyl,
$R^2$ and $R^3$ are identical or different and represent hydrogen, halogen, hydroxyl, amino, alkylamino, alkyl, alkoxy, aralkyl or aryl and
Me denotes an alkali metal.

Furthermore a process for the preparation of the said alkali metal salts of hydroxybenzoates, which are substantially anhydrous and free from hydrobenzoic acid, characterized in that a solution or suspension of a hydroxybenzoate of the formula

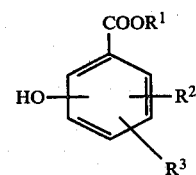

in which $R^1$, $R^2$ and $R^3$ have the abovementioned meaning, is neutralized with an alkali metal hydroxide at $-10°$ to $+50°$ C. until the degree of neutralization is 0.95 to 1.05, a degree of neutralization of 1.00 denoting the end point of the neutralization of the phenolic OH group by the alkali metal hydroxide, and the resulting solution or suspension of the alkali metal salt of the hydroxybenzoate is passed to a mild drying operation which does not damage the product and is in itself known, after a time such that the content of hydroxybenzoic acid or the alkali metal salt thereof in this solution or suspension does not reach the value of 1% by weight, relative to the amount of alkali metal salt of hydroxybenzoate contained in this solution or suspension.

5 Claims, No Drawings

PROCESS FOR THE PREPARATION OF ALKALI METAL SALTS OF HYDROXYBENZOATES, WHICH ARE SUBSTANTIALLY ANHYDROUS AND FREE FROM HYDROXYBENZOIC ACID

The invention relates to alkali metal salts of hydroxybenzoates, which are substantially anhydrous and free from hydroxybenzoic acid, and a process for their preparation.

It is known to prepare the alkali metal salts of hydroxybenzoates by bringing together an ethereal solution of the ester and a concentrated methanolic solution of an alkali metal hydroxide (Archiv der Pharmazie 267, 684 (1929)). This process, which is evidently uneconomical and, because of the flammability of the solvents, dangerous, gives the alkali metal salts of lower alkyl esters of 4-hydroxybenzoic acid in a not completely anhydrous form and cannot be applied at all to higher esters (German Reichs-patent No. 713,690).

It is furthermore known to prepare anhydrous alkali metal salts of hydroxybenzoates by reacting a hydroxybenzoate with an alkali metal phenolate in an inert organic solvent (German Offenlegungsschrift No. 2,044,705). A prerequisite of this process is the preparation of an anhydrous alkali metal phenolate, and the process leads to products which are unsuitable as an additive to foodstuffs (U.S. Pat. No. 2,046,324) because of possible contamination by physiologically unacceptable organic solvents, such as, for example, aromatic hydrocarbons, and by phenol, which has a low volatility and is etching.

It is also known to prepare alkali metal salts of hydroxybenzoates by intimately mixing the ester with an equivalent amount of solid alkali metal hydroxide, only a little water being added. A viscous state is thereby maintained until, as a result of the heat of neutralisation, the water has evaporated. (German Reichspatent No. 713,690). In this procedure, however, there is a danger that, in the viscous state, the ester group of the hydroxybenzoate will be saponified by the water, under the influence of the heat of neutralisation. (German Auslegeschrift No. 1,907,230).

In another process for obtaining alkali metal salts of a hydroxybenzoate, the neutralisation in water is carried out at a low temperature and a hydrate of the alkali metal salt of the hydroxybenzoate is separated out, dried and, at a temperature which is increased only slowly, is dehydrated in a manner such that the hydrate does not melt (German Auslegeschrift No. 1,907,230). Yields of about 60% of the theoretical yield are obtained in this process. Long drying times of 11 to 18 hours are necessary.

The invention relates to alkali metal salts of hydroxybenzoate, which are substantially anhydrous and free from hydroxybenzoic acid and have the formula (I)

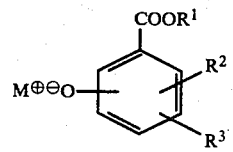

in which
$R^1$ denotes alkyl, alkenyl, cycloalkyl or aralkyl,
$R^2$ and $R^3$ are identical or different and represent hydrogen, halogen, hydroxyl, amino, alkylamino, alkyl, alkoxy, aralkyl or aryl and
M denotes an alkali metal.

Examples of alkyl radicals which may be mentioned are those with 1–20 carbon atoms, such as methyl, ethyl, propyl, isopropyl, butyl, isobutyl, hexyl, heptyl, octyl, isooctyl, decyl, dodecyl, hexadecyl or eicosyl. Alkyl radicals with 1–8 carbon atoms are preferred, and those with 1–4 carbon atoms are very particularly preferred.

Examples of alkenyl radicals which may be mentioned are those with 3–8 carbon atoms, such as allyl, butenyl, hexenyl and octenyl. Alkenyl radicals with 3–4 carbon atoms are preferred, and the allyl radical is particularly preferred.

Examples of cycloalkyl radicals which may be mentioned are those with 4–8 carbon atoms, such as cyclobutyl, cyclopentyl, cyclohexyl, cycloheptyl and cyclooctyl. Preferred cycloalkyl radicals are those with 5–6 carbon atoms.

Examples of aralkyl radicals which may be mentioned are those with 1–2 carbon atoms in the aliphatic part and 6–12 carbon atoms in the aromatic part, such as benzyl, phenylethyl and biphenylmethyl. Preferred aralkyl is benzyl.

Examples of halogen which may be mentioned are fluorine, chlorine, bromine and iodine, preferably chlorine and bromine.

Examples of alkylamino substituents which may be mentioned are those with 1 to 4 carbon atoms, such as methylamino, dimethylamino, ethylamino, diethylamino, propylamino and butylamino.

Examples of alkoxy substituents which may be mentioned are those with 1–4 carbon atoms, such as methoxy, ethoxy, propoxy and butoxy.

Examples of aryl substituents which may be mentioned are those with 6–12 carbon atoms, such as phenyl, biphenyl or naphthyl. Preferred aryl is phenyl.

Aromatic substituents can in turn be substituted, by hydroxyl, amino or halogen, for example fluorine, chlorine, bromine or iodine.

Examples of alkali metals which may be mentioned are sodium, potassium and lithium, preferably sodium and potassium, and particularly preferably sodium.

Examples which may be mentioned of alkali metal salts of hydroxybenzoates which are substantially anhydrous are those which contain not more than 5% by weight, preferably not more than 2% by weight and particularly preferably not more than 0.5% by weight of water.

Examples which may be mentioned of alkali metal salts of hydroxybenzoates, which are substantially free from hydroxybenzoic acid, are those which contain not more than 3% by weight of hydroxybenzoic acid or the alkali metal salt thereof. Preferred substances of the formula (I) are those which contain not more than 1% by weight of hydroxybenzoic acid or the alkali metal salt thereof, and those which contain not more than 0.35% by weight are particularly preferred.

A process for the preparation of alkali metal salts of hydroxybenzoates, which are substantially anhydrous and free from hydroxybenzoic acid and have the formula (I)

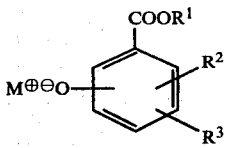

(I)

in which
R¹ denotes alkyl, alkenyl, cycloalkyl or aralkyl,
R² and R³ are identical or different and represent hydrogen, halogen, hydroxyl, amino, alkylamino, alkyl, alkoxy, aralkyl or aryl and
M denotes an alkali metal,
has also been found, and is characterised in that a solution or suspension of a hydroxybenzoate of the formula (II)

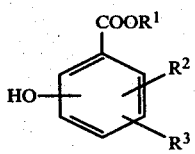

(II)

in which R¹, R² and R³ have the abovementioned meaning, is neutralised with an alkali metal hydroxide at −10° to +50° C. until the degree of neutralisation is 0.95 to 1.05, a degree of neutralisation of 1.00 denoting the end point of the neutralisation of the phenolic OH group by the alkali metal hydroxide, and the resulting solution or suspension of the alkali metal salt of the hydroxybenzoate is passed to a mild drying operation which does not damage the product and is in itself known, after a time such that the content of hydroxybenzoic acid or the alkali metal salt thereof in this solution or suspension does not reach the value of 1% by weight, relative to the amount of alkali metal salt of hydroxybenzoate contained in this solution or suspension.

Hydroxybenzoates which are preferably used for the preparation of a solution or suspension of their alkali metal salts are those of the formula (II)

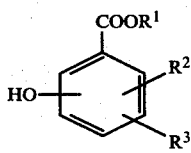

(II)

in which
R¹ denotes alkyl, allyl, cyclohexyl or benzyl and
R² and R³ are identical or different and represent hydrogen, chlorine, bromine, hydroxyl, methyl or methoxy.

Hydroxybenzoates which are very particularly preferred for use in the preparation of a solution or suspension of their alkali metal salts are those of the formula (II) in which
R¹ denotes alkyl, allyl, cyclohexyl or benzyl and
R² and R³ represent hydrogen.

Examples of hydroxybenzoates which can be employed according to the invention are: the methyl, ethyl, propyl, isopropyl, butyl, isobutyl, allyl, cyclopentyl, cyclohexyl and benzyl esters of 2-hydroxy-, 3-hydroxy-, 4-hydroxy-, 3-methyl-2-hydroxy-, 2-hydroxy-3-methyl-5-chloro-, 2-hydroxy-5-tert.-butyl-, 2,4-dihydroxy-, 2-hydroxy-3-methoxy-, 3-amino-4-hydroxy-, 4-amino-2-hydroxy-, 5-chloro-2-hydroxy-, 3,5-dihydroxy and 3-chloro-4-hydroxy-benzoic acid.

Hydroxybenzoates are known and can be prepared, for example, by esterifying hydroxybenzoic acids with suitable alcohols (J. Org. Chem. 2, 253 (1937); and Houben-Weyl, Methoden der organischen Chemie (Methods of Organic Chemistry), Volume VIII, pages 468, 525 and 544, Georg-Thieme-Verlag, Stuttgart (1952)).

Examples which may be mentioned of alkali metal hydroxides for neutralising the hydroxybenzoates are lithium hydroxide, sodium hydroxide and potassium hydroxide, preferably sodium hydroxide and potassium hydroxide and particularly preferably sodium hydroxide.

Solvents or suspending agents which may be mentioned are those in which the desired salt formation to give the phenolic OH group takes place without the solvents or suspending agents themselves being changed under the reaction conditions for the salt formation or during the subsequent drying, examples being lower aliphatic alcohols, water or mixtures of lower aliphatic alcohols and water. Lower aliphatic alcohols which may be mentioned in particular are those with 1-4 carbon atoms, such as methanol, ethanol, propanol, isopropanol, butanol, iso-butanol and tert.-butanol. Water is the particularly preferred solvent or suspending agent, from economical, ecological and safety considerations.

The neutralisation is carried out in the temperature range from −10° C. to +50° C., preferably in the range from +15° to +25° C.

The concentration of the alkali metal salt of a hydroxybenzoate in the solution or suspension in which the neutralisation is carried out and which is passed to the drying can be 10-80% by weight, preferably 25-60% by weight.

In a preferred embodiment of the process according to the invention, the concentration of the hydroxybenzoate is adjusted such that a solution is formed in the course of the neutralisation. In this case, the concentration, in the solution, of the alkali metal salt of a hydroxybenzoate can be, for example, 0.5 to 10, preferably 1 to 5%, by weight below the particular saturation concentration.

In the process according to the invention, a solution or suspension of a hydroxybenzoate is neutralised until the degree of neutralisation is 0.95 to 1.05, a degree of neutralisation of 1.00 denoting the point at which the amount of phenolic OH group and the amount of alkali metal hydroxide are exactly equivalent to one another.

A degree of neutralisation of 0.97 to 1.03 is preferred, and a degree of neutralisation of 0.98 to 1.00 is particularly preferred.

The operation in which the dissolved or suspended hydroxybenzoate is neutralised can be carried out in one or two stages. The procedure can be discontinuous or continuous. In the case of a two-stage neutralisation, the two stages can be independently of one another carried out discontinuously or continuously.

In the case of a single-stage neutralisation and if the hydroxybenzoate is in suspension at the start of the neutralisation, the pH must in general be controlled continuously whilst the alkali metal hydroxide is added. This ensures that at no time is alkali metal hydroxide present in excess, relative to the dissolved hydroxybenzoate. If the alkali metal hydroxide is added at a rate higher than that at which the suspended hydroxybenzoate dissolves, such a high pH value is established that the alkali metal salt of the hydroxybenzoate which is present in solution already suffers noticeable saponification to give the hydroxybenzoic acid or salt thereof during the neutralisation.

In the case of a two-stage neutralisation, it is possible because of the relatively high rate of solution at lower degrees of neutralisation, to add most of the alkali metal hydroxide required for complete neutralisation to the suspension of the initially introduced hydroxybenzoate without controlling the pH, of this addition is carried out uniformly over not too short a period of time. In general, the alkali metal hydroxide is added over a period in the range from about 10 to 40 minutes.

A preferred variant of the process according to the invention consists in carrying out the neutralisation in two stages, a degree of neutralisation of 0.90 to 0.97, preferably 0.94 to 0.96, being achieved in the first stage and the neutralisation being brought to completion in the second stage.

At the preferred high concentrations, close to the saturation concentration, hydroxybenzoates are very much more readily soluble in an aqueous solution of their alkali metal salts than in water. Thus, for example, complete solution of the initially suspended hydroxybenzoate can be achieved at a degree of neutralisation of 0.90 to 0.97 and at a suitable concentration, which depends on the substances, the solution containing hydroxybenzoate which has not yet been neutralised. For example, n-propyl 4-hydroxybenzoate is more than 100 times more readily soluble in a solution of its sodium salt than in water.

The solution with a degree of neutralisation of 0.90 to 0.97 can be completely neutralised immediately before the intended drying, and if appropriate after intermediate storage, which becomes necessary in industrial processes.

The pH of this second neutralisation stage should be monitored, but the neutralisation can be carried out as rapidly as desired since it proceeds as an ionic reaction in a homogeneous phase.

Immediately after completion of the neutralisation of hydroxybenzoates in two stages, a significantly lower content of hydroxybenzoic acid is observed than in the case of a neutralisation in only one stage.

The solution or suspension, prepared according to the invention, of an alkali metal salt of a hydroxybenzoate is subjected to a mild drying, which does not damage the product, to obtain the alkali metal salts of the hydroxybenzoate which are substantially anhydrous and free from hydroxy benzoic acid. Convection drying processes or contact drying processes which do not damage the product are signified, for example, by short drying times, low drying temperatures and removal of the solvent or suspending agent under vacuum, or by a combination of such characteristics, and are known to the expert.

The drying operation can be carried out, for example, in a spray-drier of the customary construction with an open or closed gas system, in an oxygen-free or oxygen-containing atmosphere in the customary inlet-temperature range from about 130° to 250° C. with the customary difference in temperature, between the gas inlet and gas outlet, of about 50° to 200° C.

However, it is also possible to carry out drying by thin film contact drying on a drum drier under normal or reduced pressure, preferably under reduced pressure vacuum, at customary heating agent temperatures of, for example, 80° to 180° C. In the case of vacuum drum drying, the customary pressures can be applied preferably below 100 mbars.

However, drying can also be carried out by thick film contact drying under vacuum, in a drier in which the product is tumbled. In this case also, customary heating agent temperatures, for example 80° to 180° C., and customary pressures, for example below 100 mbars, can be applied.

The alkali metal salt of the hydroxybenzoate leaves the drier as a substantially anhydrous substance, that is to say, in the sense according to the invention, with a water content in the dried alkali metal salt of the hydroxybenzoate of not more than 5% by weight, preferably not more than 2% by weight and particularly preferably not more than 0.5% by weight.

A solution or suspension of an alkali metal salt of a hydroxybenzoate with a degree of neutralisation of less than 1.00 contains a small amount of hydroxybenzoate with a free phenolic OH group. Such hydroxybenzoates have low melting points, sometimes of below 100° C. (Ullmann's Enzyklopädie der Technischen Chemie (Ullman's Encyclopaedia of Industrial Chemistry), Volume 13, pages 90 and 93, Urban & Schwarzenberg, Munich/Berlin, 1962). It was to be expected that, at the customary high drying temperatures, a small proportion of 1–2% of hydroxybenzoate with a free phenolic OH group would lead to the dried particles sticking together and hence to encrustations in the drying equipment. Whilst this expectation also applies to an ever greater extent in the case of a degree of neutralisation of less than 0.95 and depends on the nature of the ester, in particular on its melting point, it is surprisingly possible, by the process according to the invention, to convert solutions or suspensions of an alkali metal salt of a hydroxybenzoate with a degree of neutralisation of 0.95 to 1.00, preferably 0.97–1.00 and particularly preferably 0.98–1.00 into a dried product which is not tacky.

According to the invention, the solution or suspension of an alkali metal salt of a hydroxybenzoate is passed to a mild drying operation, which does not damage the product, after a time such that the content of hydroxybenzoic acid or alkali metal salt thereof in this solution or suspension does not reach the value of 1% by weight, relative to the amount of alkali metal salt, of the hydroxybenzoate, which is contained in this solution or suspension. The solution or suspension of an alkali metal salt of a hydroxybenzoate is preferably passed to the mild drying operation, which does not damage the product, after a time such that the content of hydroxybenzoic acid or the alkali metal salt thereof in this solution or suspension reaches a value of 0.01 to 0.95% by weight, particularly preferably 0.03 to 0.5% by weight, relative to the amount of alkali metal salt, of the hydroxybenzoate, which is contained in this solution or suspension. In the sense of the concept of the invention, as low as possible a content of hydroxybenzoic acid or alkali metal salt thereof in this solution or suspension is of course aimed for.

Timely feeding of the neutralised solution or suspension of an alkali metal salt of a hydroxybenzoate in the sense of the concept of the invention is linked with the other characteristics of the process according to the invention, for example with the temperature, the degree of neutralisation or the concentration. For example, in a 50% strength aqueous solution of the sodium salt of n-propyl 4-hydroxy-benzoate with a degree of neutralisation of 0.95 at 20° C., the limiting value, which gives rise to a content of 4-hydroxybenzoic acid, or of the sodium salt thereof, of 1% by weight in the dried sodium salt of n-propyl 4-hydroxybenzoate, is reached only after 15 days. If the neutralisation is carried out at a higher temperature, for example up to 50° C., and up to a higher degree of neutralisation, for example up to a degree of neutralisation of 1.05, timely feeding of the neutralised solution or suspension to the drying process means a period of, for example, 1 to 12 hours. The fact that a solution or suspension of an alkali metal salt of a hydroxybenzoate which has been neutralised up to a degree of neutralisation of, for example, 0.95 at a low temperature, for example 20° C., can be dried by processes other than the drying processes described is of course also within the concept of the invention, and these other drying processes can optionally also be characterised by longer drying times and/or increased drying temperatures.

It is surprising that, in the process according to the invention, the alkali metal salts of the hydroxybenzoates can be dried from a solution or suspension and are thereby obtained substantially free from hydroxybenzoic acid, although it is known that in solutions of an alkali salt of a hydroxybenzoate the ester group is rapidly saponified at elevated temperature (German Auslegeschrift No. 1,907,230).

It is also surprising that solutions of an alkali metal salt of a hydroxybenzoate with a degree of neutralisation of up to 1.00, preferably of 0.98 to 1.00, can be dried under the conditions mentioned without the proportion of the hydroxybenzoate which is not bonded by salt formation at the phenolic OH group leading to the dried particles sticking together and thus to encrustations in the drying equipment.

The alkali metal salts of hydroxybenzoates are used in the preparation of raw materials for synthetic fibres (German Offenlegungsschrift No. 2,044,705), in the preparation of alkaline earth metal salts and other metal salts of hydroxybenzoates (U.S. Pat. No. 2,046,324; and Swedish Patent No. 120,451), and, on the basis of their microbicidal action, as additives to foodstuffs, pharmaceuticals, cosmetics and other animal and vegetable products endangered by microbial infection (U.S. Pat. No. 2,046,324).

The Use of Additives Regulations of 20.12.1977 (Federal Law Gazette 1/1977, page 2653 et seq.) contains statements with regard to the content of non-esterified hydroxybenzoic acid in hydroxybenzoates used as additives to foodstuffs. For example, the regulations mentioned prescribe a maximum content of p-hydroxybenzoic acid of 0.35% by weight in the relevant ethyl and n-propyl esters and of 0.7% by weight in the relevant methyl ester.

EXAMPLE 1

873.3 g of methyl 4-hydroxybenzoate were suspended in 2,000 ml of water and neutralised at 20° C. with 301 ml of 50% strength sodium hydroxide solution, the sodium hydroxide solution, towards the end of the addition, being metered in slowly at a rate such that the pH value of 12.1 established after complete neutralisation was never exceeded. Half of the solution thus obtained, after about 90 minutes, was dried immediately in a spray-drier at an air inlet temperature of 220° C. and an air outlet temperature of 130° C. (a). The second half of the solution was passed to the spray-drier after being kept at a temperature of 20° C. for 92 hours (b). The sodium salt of methyl 4-hydroxybenzoate is obtained with a 4-hydroxybenzoic acid content of 0.4% by weight and a water content of 1.3% by weight in case (a) and with a 4-hydroxybenzoic acid content of 2.5% by weight and a water content of 4.2% by weight in case (b).

EXAMPLE 2

456.6 g of methyl 4-hydroxybenzoate were suspended in 1,050 ml of water and neutralised at 20° C. with 157 ml of 50% strength sodium hydroxide solution in two stages. In the first stage, 95% of the sodium hdyroxide solution was added in the course of 30 minutes. After keeping the solution at 20° C. for 97 hours and after adding the remaining 5% of sodium hydroxide solution, it was dried in a spray-drier. The salt leaving the drier at a temperature of about 80° to 120° C. is hygroscopic and is cooled and packaged with exclusion of atmospheric moisture. The content of 4-hydroxybenzoic acid in the sodium salt of methyl 4-hydroxybenzoate is 0.5% by weight and the water content is 1.9% by weight.

EXAMPLE 3

304.4 g of methyl 4-hydroxybenzoate were suspended in 700 ml of water, and 100 ml of 50% strength sodium hydroxide solution were added in the course of 20 minutes. As soon as everything had dissolved, after a further 20 minutes, a further 4 ml of 50% strength sodium hydroxide solution was added dropwise, whereby a degree of neutralisation of 0.99 was achieved, at a pH value of 11.5. After spray-drying in a laboratory spray-drier, the 4-hydroxybenzoic acid content in the sodium salt of methyl 4-hydroxybenzoate was 0.2% by weight and the water content was 0.2% by weight.

EXAMPLE 4

891 g of n-propyl 4-hydroxybenzoate were neutralised in 712 ml of water with 260 ml of 50% strength sodium hydroxide solution in two stages. After the first stage of the neutralisation (247 ml of sodium hydroxide solution), the resulting clear solution was kept at 20° C. for 96 hours. When the neutralisation had been completed (13 ml of sodium hydroxide solution), spray-drying resulted in a product with a 4-hydroxybenzoic acid content of 0.1 percent by weight and a water content of 0.3% by weight.

EXAMPLE 5

498 g of ethyl 4-hydroxybenzoate were suspended in 874 ml of water, and 150 ml of 50% strength sodium hydroxide solution were added at 18°-20° C. in the course of 30 minutes, up to a degree of neutralisation of 0.95. After a further 20 minutes, when a clear solution was present, further 4% strength sodium hydroxide solution (6 ml) was added, whilst stirring.

Spray-drying which followed immediately, gave the sodium salt of ethyl 4-hydroxybenzoate with a 4-hydroxybenzoic acid content of 0.05 percent by weight and a water content of 1.5 percent by weight.

EXAMPLE 6

304.4 g of methyl 4-hydroxybenzoate were suspended in 740 ml of water and dissolved at 20° C. by adding 142 ml of 50% strength potassium hydroxide solution in the course of 20 minutes. Neutralisation was completed (pH 12.1) with a further 6 ml of the 50% strength potassium hydroxide solution. Spray-drying gave the pure-white potassium salt of methyl 4-hydroxybenzoate with a 4-hydroxybenzoic acid content of 0.2% by weight and a water content of 0.1% by weight.

EXAMPLE 7

152.2 g of methyl 4-hydroxybenzoate were suspended in 1,385 ml of water, and 44.3 g of solid lithium hydroxide hydrate with a LiOH content of 54% were added in portions, whilst cooling to 18°–20° C., the addition being interrupted after 42 g of lithium hydroxide hydrate had been added, until everything had completely dissolved. The pure-white lithium salt of methyl 4-hydroxybenzoate was obtained from the solution, which had a pH value of 12.0, by spray-drying and had a 4-hydroxybenzoic acid content of 0.4% by weight and a water content of 4.6% by weight.

EXAMPLE 8

77.2 g of 49.2% strength sodium hydroxide solution were added to 250 g of 2-ethylhexyl 4-hydroxybenzoate in 577 ml of water at 20° C. in the course of 35 minutes, and when a clear, somewhat viscous solution was present, the pH was brought to 12.6 with 4.1 g of 49.2% strength sodium hydroxide solution. The yellowish product obtained after spray-drying contains 0.3% by weight of 4-hydrobenzoic acid and 1.6% by weight of water.

EXAMPLE 9

114 g of benzyl 4-hydroxybenzoate were suspended in 263 ml of water and dissolved in 20 minutes with 38.6 g of 49.2% strength sodium hydroxide solution, a temperature of 20° C. being maintained, and the pH was adjusted to 12.5 with 2.0 g of 49.2% strength sodium hydroxide solution. The colourless sodium salt of benzyl 4-hydroxybenzoate, which was obtained by spray-drying, contains 0.3% by weight of 4-hydroxybenzoic acid and 1.3% by weight of water.

EXAMPLE 10

996 g of ethyl 4-hydroxybenzoate were suspended in 1,748 ml of water, and 300 ml of 50% strength sodium hydroxide solution were added at 18°–20° C. in the course of 30 minutes, up to a degree of neutralisation of 0.95. 12 ml of 4% strength sodium hydroxide solution were added, whilst stirring, to the solution which had formed after 20 minutes. The solution was dried in a vacuum twin-drum drier under a pressure of 17 mbars and at a heating agent temperature of 140° C. The sodium salt of ethyl 4-hydroxybenzoate, which is obtained in the form of flakes, has a 4-hydroxybenzoic acid content of 0.4% by weight and a water content of 0.1% by weight.

EXAMPLE 11

15.2 kg of methyl 4-hydroxybenzoate were suspended in 34.8 l of water, and 5 l of 50% strength sodium hydroxide solution (95% of the calculated amount) were added at 10° to 20° C. in the course of 30 minutes. The remaining 0.23 l of 50% strength sodium hydroxide solution was added, whilst stirring, to the solution formed, up to a pH value of 11.8. The solution thus prepared was dried on a twin-drum drier under normal pressure and at a heating agent temperature of 140° C. The end product has a 4-hydroxybenzoic acid content of 1.0% by weight and a water content of 4.7% by weight.

EXAMPLE 12

The solution of the sodium salt of methyl 4-hydroxybenzoate, prepared as in Example 11, was evaporated in a thick film contact drier (paddle drier) under a pressure of 40–20 mbars and at a heating agent temperature of 70°–90° C. The product contained 0.2% by weight of 4-hydroxybenzoic acid and 0.03% by weight of water.

What is claimed is:

1. Process for the preparation of alkali metal salts of hydroxybenzoates, which are substantially anhydrous and free from hydroxybenzoic acid and have the formula

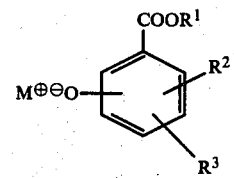

in which
R$^1$ denotes alkyl, alkenyl, cycloalkyl or aralkyl,
R$^2$ and R$^3$ are identical or different and represent hydrogen, halogen, hydroxyl, amino, alkylamino, alkyl, alkoxy, aralkyl or aryl and
M denotes an alkali metal,
characterised in that a solution or suspension of a hydroxybenzoate of the formula

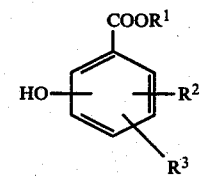

in which R$^1$, R$^2$ and R$^3$ have the abovementioned meaning, is neutralised with an alkali metal hydroxide at −10° to +50° C. until the degree of neutralisation is 0.95 to 1.05, a degree of neutralisation of 1.00 denoting the end point of the neutralisation of the phenolic OH group by the alkali metal hydroxide, and the resulting solution or suspension of the alkali metal salt of the hydroxbenzoate is passed to a mild drying operation which does not damage the product and is in itself known, after a time such that the content of hydroxybenzoic acid or the alkali metal salt thereof in this solution or suspension does not reach the value of 1% by weight, relative to the amount of alkali metal salt of hydroxybenzoate contained in this solution or suspension.

2. Process according to claim 2, characterized in that water is used as the solvent or suspending agent.

3. Process according to claims 1 and 2, characterised in that the concentration of the solution or suspension of the alkali metal salt of the hydroxybenzoate which is passed to the drying operation is adjusted to 10 to 80% by weight.

4. Process according to claims 1 to 3, characterised in that the concentration of the solution of the alkali metal salt of the hydroxybenzoate which is passed to the drying operation is adjusted to 0.5 to 10% by weight below the saturation concentration.

5. Process according to claims 1 to 3, characterised in that, in a first stage, the solution or suspension of the hydroxybenzoate is treated with alkali metal hydroxide up to a degree of neutralisation of 0.90 to 0.97 and the neutralisation is brought to completion in a second stage.

* * * * *

UNITED STATES PATENT AND TRADEMARK OFFICE
CERTIFICATE OF CORRECTION

PATENT NO. : 4,276,431
DATED : Jun. 30, 1981
INVENTOR(S) : Peter Schnegg et al

It is certified that error appears in the above-identified patent and that said Letters Patent are hereby corrected as shown below:

Column 10, line 51   Delete "2" and insert --1--.

Signed and Sealed this

Twenty-seventh Day of October 1981

[SEAL]

Attest:

GERALD J. MOSSINGHOFF

*Attesting Officer*   *Commissioner of Patents and Trademarks*